(12) United States Patent
Walderich et al.

(10) Patent No.: US 6,465,169 B2
(45) Date of Patent: Oct. 15, 2002

(54) METHOD FOR CRYOCONSERVATION OF ZEBRAFISH SPERM

(75) Inventors: Brigitte Walderich, Tübingen (DE); Renate Nordin, Tübingen (DE)

(73) Assignee: Artemis Pharmaceuticals GmbH, Köln (DE)

( * ) Notice: Subject to any disclaimer, the term of this patent is extended or adjusted under 35 U.S.C. 154(b) by 0 days.

(21) Appl. No.: 09/741,282

(22) Filed: Dec. 19, 2000

(65) Prior Publication Data

US 2001/0023060 A1 Sep. 20, 2001

Related U.S. Application Data

(60) Provisional application No. 60/183,303, filed on Feb. 17, 2000.

(30) Foreign Application Priority Data

Jan. 14, 2000 (EP) .............................................. 00100720

(51) Int. Cl.$^7$ .............................. A01N 1/02; C12N 5/00; C12N 5/22

(52) U.S. Cl. .............................. 435/2; 435/374; 435/325
(58) Field of Search .................................. 435/374, 325, 435/2

(56) References Cited

PUBLICATIONS

Harvey et al. Cryopreservation of zebra fish spermatozoa using methanol. Can. J. Zool. 1982. 60:1867–1870.*
Aoki et al. Cryopreservation of medaka spermatozoa. Zoological Science. 1997. 14;641–644.*
F.G.Ransom, et al.; Collection, Storage, and Use of Zebrafish Sperm; Methods of Cell Biology, vol. 60; 1999; pp. 365–372.

* cited by examiner

*Primary Examiner*—Irene Marx
*Assistant Examiner*—Vera Afremova
(74) *Attorney, Agent, or Firm*—Sarah Elson; Jan P. Brunelle

(57) ABSTRACT

A method for cryoconservation of Zebrafish sperm, and Zebrafish sperm obtained by said method.

18 Claims, 5 Drawing Sheets

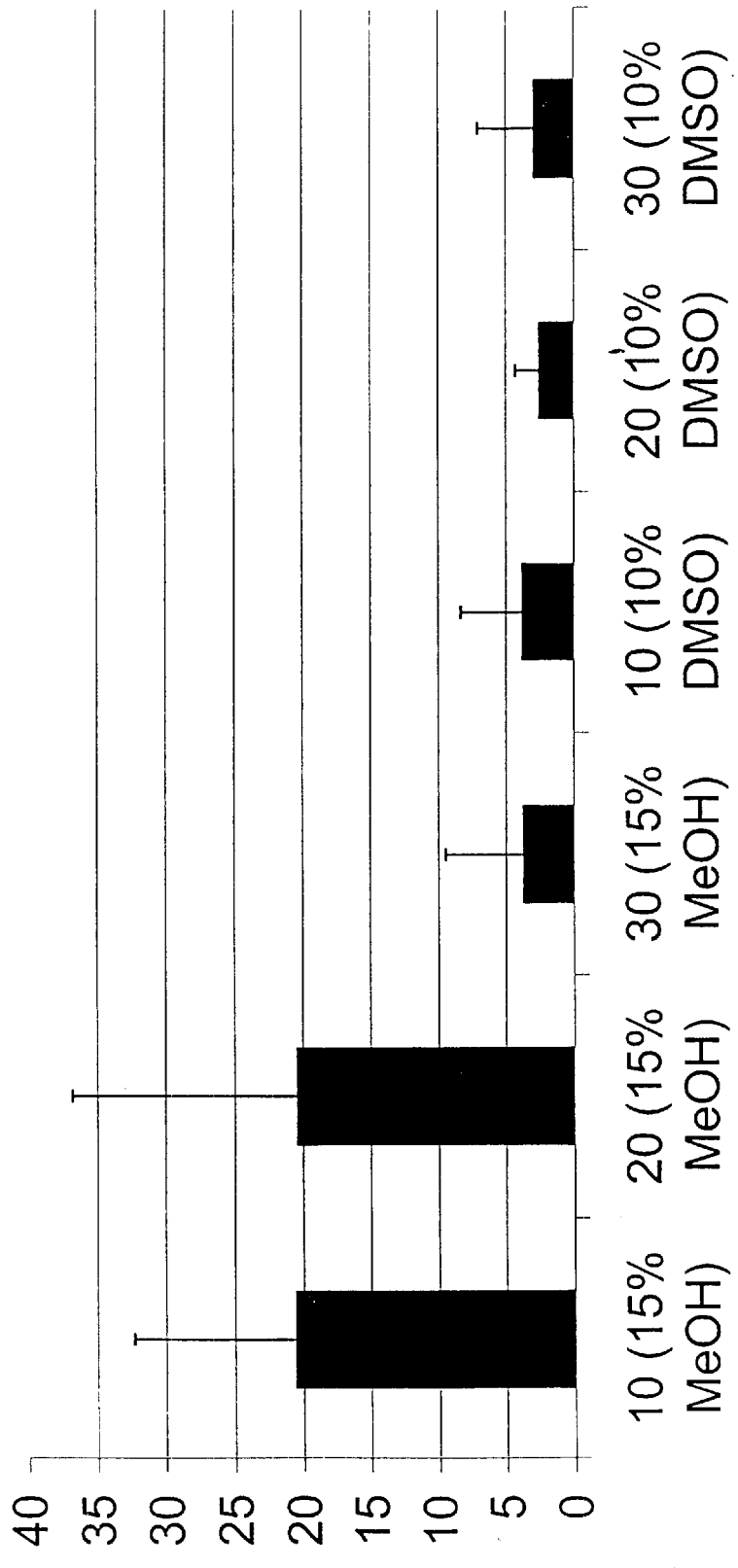

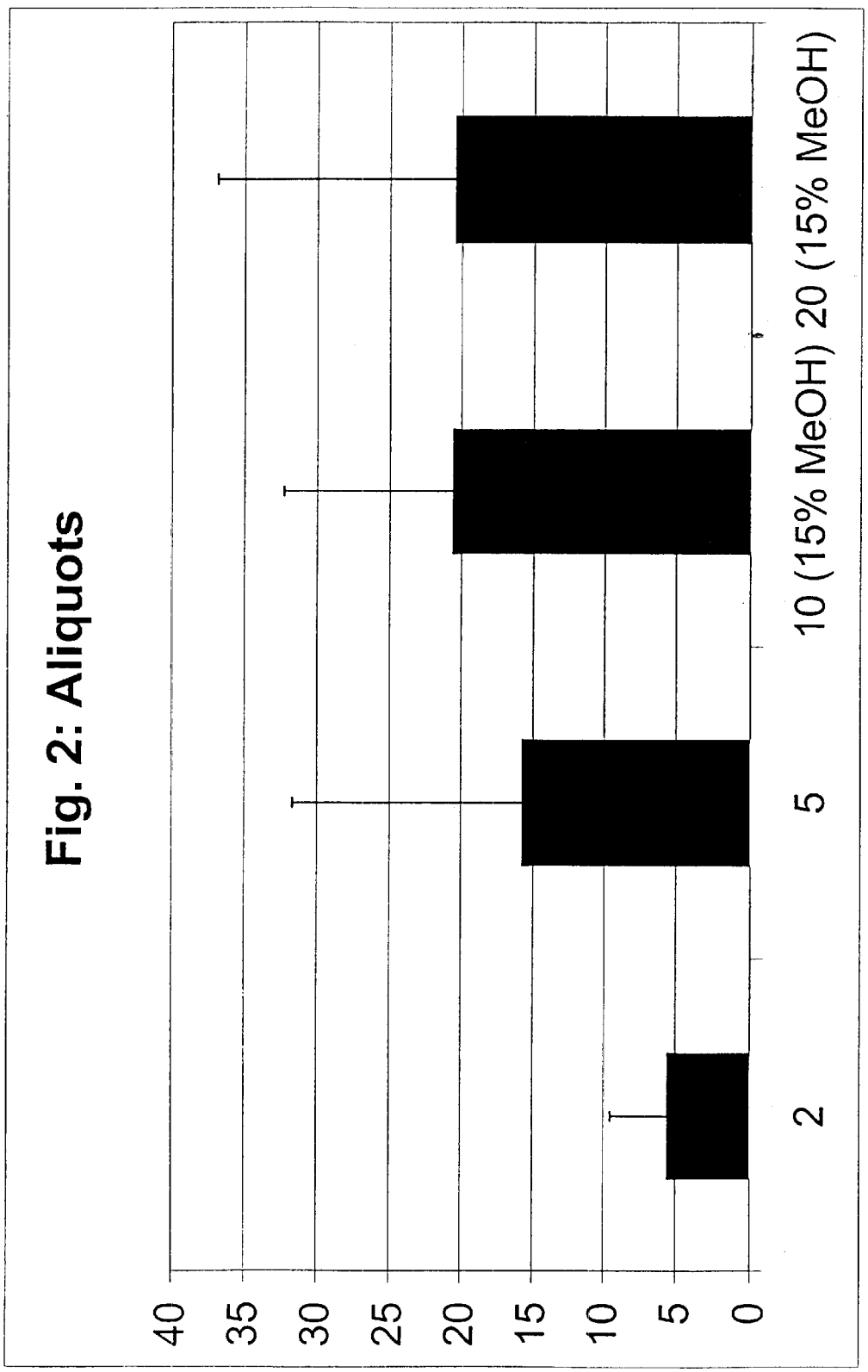

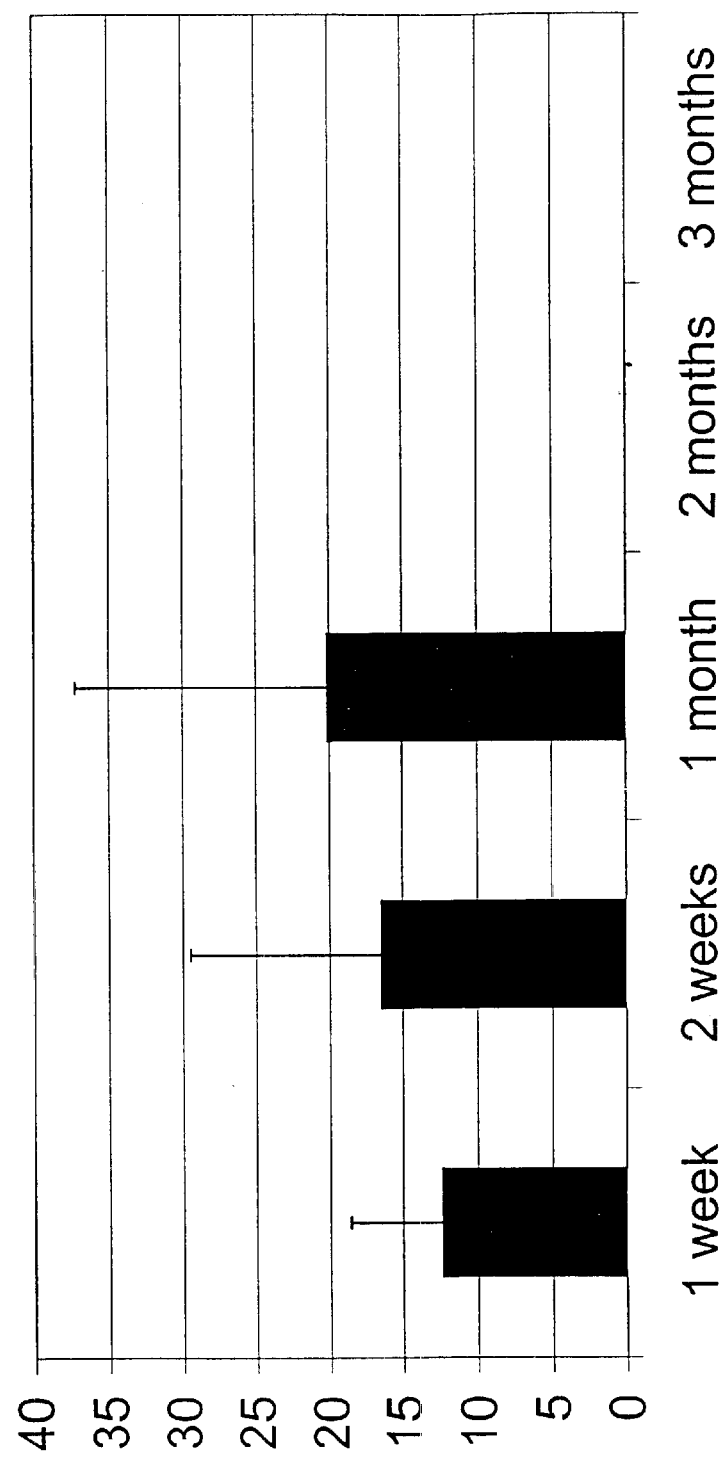
Fig. 3: Long term storage

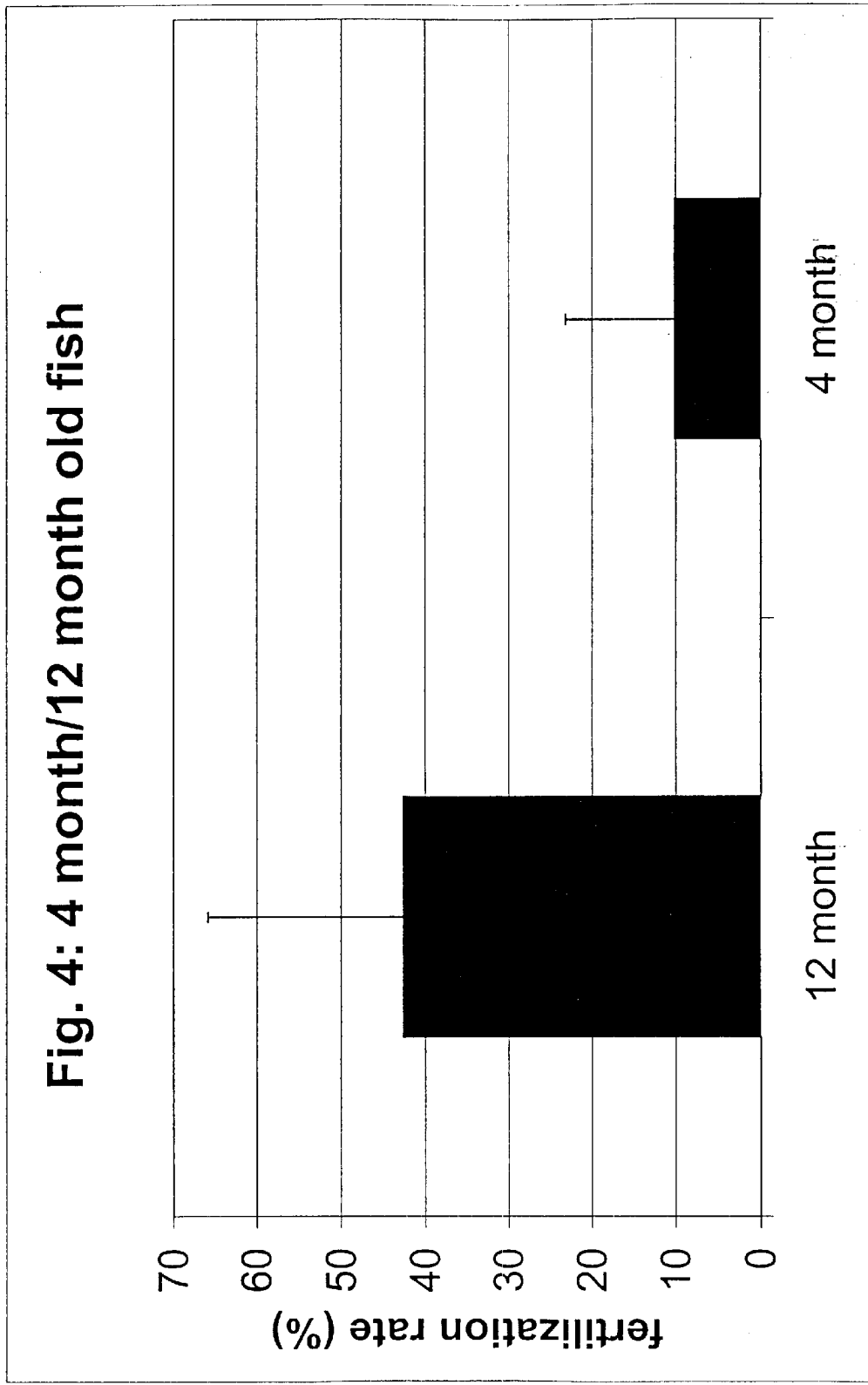

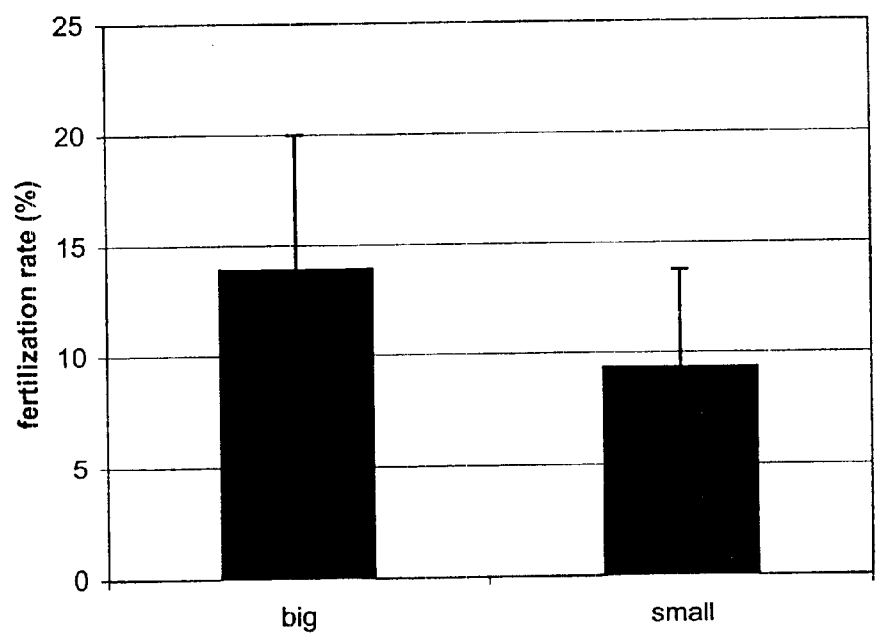

METHOD FOR CRYOCONSERVATION OF ZEBRAFISH SPERM

CROSS-REFERENCE TO RELATED APPLICATIONS

This application claims priority of U.S. provisional application serial No. 60/183,303 filed on Feb. 17, 2000, the entire disclosure of which is incorporated herein by reference.

BACKGROUND OF THE INVENTION

The present invention provides a method for cryoconservation of Zebrafish sperm, and samples of Zebrafish sperm obtainable by said method.

Zebrafish sperm can be prepared by two different methods for cryoconsevation and In Vitro Fertilization (IVF) of Zebrafish eggs:

1. Sperm can be squeezed directly from male fish and frozen in cryoprotectant.
2. Sperm can be isolated from prepared fish testis and frozen in cryoprotectant. (Ransom & Zon, Methods in Cell Biology, Vol. 60, p. 365–372, (1999)). Said method comprises homogenizing the testis by using a Kontes pellet pestle.

Method 1 is established and functions, however, it has several disadvantages:

- About 50% of all fish give no sperm sample by using the squeezing procedure.
- Such fish can be squeezed again after 2 weeks: This needs space and time.
- The recovered sperm has a volume of 0.5–2 $\mu$l, resulting in only one aliquot of sperm per squeezing, i.e. the procedure has to be repeated several times.
- The squeezed sperm can differ very much in quality yielding fertilization rates between 0–50%.

Method 2 has been described to function in a protocol obtained from Ransom & Zon, 1999, however we have not been able to reproduce it. This method would have several advantages in comparison to the squeezing method:

- Sperm samples can be obtained from every single fish.
- Several sperm aliquots can be frozen from one testis preparation: time and space saving.

SUMMARY OF THE INVENTION

Starting from the method of Ranson & Zon, (1999), a reliable method to freeze Zebrafish sperm prepared from testis was established. This method gives at least 2 sperm samples from one testis preparation. The new method can be done very quickly: 5 minutes per fish are needed for the sperm preparation. As demonstrated in 23 independent experiments, fertilization rates between 10–50% were observed, using fish between 4 and 12 months old.

The present invention thus provides a method for cryoconservation of Zebrafish sperm comprising (a) removing the testis from the body cavity of a male Zebrafish;
(b) rinsing the testis isolated in step (a) with a cryoprotectant to yield a sperm suspension: and
(c) freezing said sperm suspension, wherein the amount of cryoprotectant used in step (b) is such that the volume of the sperm suspension be less than 30 $\mu$l.

The present invention further provides samples of Zebrafish sperm obtained by the above method.

BRIEF DESCRIPTION OF THE SEVERAL VIEWS OF THE DRAWINGS

FIG. 1 shows the variation of the cryoprotectant and its concentration on the fertilization rate.

FIG. 2 shows the influence of the aliquot size on the fertilization rate.

FIG. 3 shows the influence of the storage time.

FIG. 4 shows the influence of the age of the male fish on the fertilization.

FIG. 5 shows the influence of the size of the fish on the fertilization rate.

DETAILED DESCRIPTION OF THE INVENTION

In the following the sperm preparation and cryoconservation is described in more detail.

Male Zebrafish are anaesthetized, dried with a tissue paper, decapitated and the testis is removed from the body cavity. It is important to dry the fish and the equipment used very well, as water may activate the sperm. Activated sperm cannot be used for successful IVFs.

The isolated testis are rinsed very carefully with about 20 $\mu$l of cryoprotectant having a temperature from 0 to 10° C., preferably 4° C., using a mikrotip.

The suspension obtained should have a volume of at least 20 $\mu$l but less than 30 $\mu$l per fish.

The cryoprotectant preferably consists of 1× Ginzkurg Ringer Solution containing 15% wt. % milkpowder and 15% methanol vol. %.

The sperm suspension can be divided into 2 to 5 aliquots, preferably into 5 $\mu$l portions in glass capillaries.

For freezing, the capillaries are cooled down in cryovials and plastic tubes to −70° C. for at least 30 minutes and are than transferred in the cryovial into liquid nitrogen, i.e., are cooled down to −196° C. (storage temperature).

The in vitro Fertilization is performed as follows:

Female Zebrafish are anaesthetized and dried very carefully.

The eggs are squeezed by pressing the belly of the female towards the anal fin.

A capillary with frozen sperm is thawed, mixed with 70 $\mu$l of Hanks final solution and given to the eggs. Incubation time: 30 seconds at room temperature.

750 $\mu$l fish water is added to the eggs and incubated 2 minutes at room temperature.

9 ml of water are added and the eggs are incubated at 28° C. for 6 hours.

The fertilized eggs are transferred into embryo-medium E3.

The following experiments were done: The method to isolate a sperm suspension from testis was altered. Ransom and Zon (1999) describe to homogenize the testis by using a Kontes pellet pestle. Since this method didn't work the sperm were isolated from the testis by flushing the testis very carefully with the cryopreservation solution on ice using different micropipette tips. The most successful method was to use 10 $\mu$l cristal tips Dimethylsulfoxide (DMSO) was tried instead of methanol, as most cryopreservation methods are using DMSO as a cryoprotectant. Methanol was more efficient compared to DMSO, as shown in the fertilization rates (see FIG. 1).

Different concentrations of DMSO and Methanol were tried: 10%, 15% and 20% of Methanol worked, 15% Methanol gave the best results, 7.5% and 10% of DMSO worked as well, however the fertilization rates obtained were lower than with 15% methanol (see FIG. 1).

Different volumes of the sperm suspension were tested: 10, 20, 30, 50, 100 and 500 µl. It was shown that sperm samples >30 µl gave low or negative results in the IVF. The optimal volume of 20 µl can be divided into 4 aliquots a 5 µl.

The cooling down protocol itself was tried to change: Ransom and Zon described that the sperm has to be frozen on crushed $CO_2$ for 30 minutes and then in liquid nitrogen. This method was shown to be the most efficient compared to freezing the sperm samples directly into liquid nitrogen or cooling down 1° C. per minute. These experiments are described in more detail below.

EXAMPLES

Material Used

- Milk powder (Carnation Nonfat Dry Milk, Nestle)
- Methanol p.a. (Merck, Darmstadt)
- DMSO Hybrimax (Sigma, München)
- RPMI 1640 (Sigma, München)
- Foetal calf serum (Life Technologies, Karlsruhe)
- Cristal tips (Eppendorf, Hamburg)
- Cryovials, 2 ml (Roth, Karlsruhe)
- 50 ml plastic tubes (screw caps) (Greiner, Nürtingen)
- MESAB Solution (0.4% ethyl-m-aminobenzoate methanesulfonate+1% $Na_2HPO_4 \times 2H_2O$, pH 7.2)
- 1×Ginzburg-Ringer-Solution (Ransom & Ron, 1999)
- Cryoprotectant solution: 1× Ginzburg-Ringer-Solution is prepared and frozen in 4.5 ml aliquots. 15% milk powder (w/v) is resolved and 15% methanol (v/v) is added. The cryoprotectant is cooled down on ice and used freshly prepared.
- Hanks Final Solution (Ranson & Zon, 1999)
- Embryo medium E3 (Haffter et al., 1996 Development 123, p. 1–36)

Example 1

It was tried to reproduce the optimal freezing conditions as described above in 23 independent experiments. In comparison to these tests, the experiments using 10% DMSO instead of 15% methanol are shown in FIG. 1. One column represents the fertilization rates of at least 6 independent IVFs. The experiments were carried out as described below.

- Male fish (4–12 months old) were anaesthetized in 4 ml of the MESAB solution per 100 ml fish water, dried very carefully using a tissue paper and decapitated.
- The testis were dissected and transferred into a Eppendorf cup filled with 20 µl of icecold cryoprotectant solution. The cryoprotection solution consisted of 1×Ginzburg Ringer Solution+15% Milk powder (w/v)+15% Methanol (v/V) or of 1×Ginzburg Ringer Solution+15% milk powder (w/v)+10% DMSO (v/v) and was prepared freshly. The testis were rinsed with the icecold solution using a micropipette with a cristal tip.
- Aliquots of 10, 20 and 30 µl were filled in capillaries and cryotubes and frozen in a 50 ml plastic tube on dry ice for 30 minutes.
- The samples in the cryovials were transferred into liquid nitrogen.
- After one week different sperm samples were used for IVF experiments.
- Female Zebrafish were anaesthetized with the MESAB solution (see above) and dried very carefully using a tissue paper.
- The eggs were squeezed by pressing the belly of the fish towards the anal fin into a petri dish.
- 1 aliquot of thawed sperm was resuspended in 70 µl of Hand's final solution, added to the eggs and incubated 30 seconds at room temperature.
- 750 µl of fish water were added and incubated 2 minutes at room temperature.
- 9 ml of fish water were added and the eggs were incubated 6 hours at 28° C.
- Fertilized eggs were separated and counted to calculate the fertilization rate. They were transferred into E3 medium. The unfertile eggs were counted and discarded.

Result: It was shown that under these conditions fertilization rates between 2 and 20% were achieved. In some cases fertilization rates up to 50% and more could be found. The experiments using 15% Methanol as a cryoprotectant gave the highest fertilization rates of 20%. 10% DMSO as cryoprotectant yielded fertilization rates lower than 3.5%. It can also be seen that preparation volumes higher than 20 µl gave lower fertilization rates.

Example 2

20 µl sperm solution, prepared as described in example 1 were 15% Methanol, were divided into several portions: 1×20 µl, 2×10 µl, 4×5 µl, 10×2 µl. These sperm samples were frozen and thawed and used for IVF as described above. 6 independent experiments were done.

Result: 20 µl of sperm solution can be divided into 5 µl portions with a similar fertilization rate as for 10 or 20 µl portions (FIG. 2). 2 µl aliquots show significantly lower fertilization rates.

Example 3

The sperm samples were prepared from 12 month old fish as described above in 10 µl portions and were thawed at different timepoints to show how long they can be stored in liquid nitrogen without loosing activity.

Result: We have thawed 4 samples of different fish after 1 week, 2 weeks and 1 month of storage. In these experiments we could not observe lower fertilization rates. (FIG. 3)

Example 4

Sperm samples were prepared as described above from 4 month and 12 month old fish and frozen in 10 µl sperm samples. These were used for IVF in 6 independent experiments as described.

Result: It could be shown that sperm of 12 month old fish yield higher fertilization rates (ca. 42%) than 4 month old fish (ca. 10%). Therefore, older fish should be taken for testis preparation rather than younger fish. (FIG. 4)

Example 5

Sperm samples were prepared as described above from 4 month old fish which differed in size. The samples were frozen in 10 µl aliquots and frozen and thawed and used for IVF as described above. 6 samples of big fish were compared to 10 samples of small fish.

Result: The samples of small fish gave lower fertilization rates (ca. 9%) compared to the big fish (ca. 14%). This means that for sperm preparation, the fish should be well fed and should be as big as possible to the timepoint were sperm is isolated. (FIG. 5)

What is claimed is:

1. A method for cryoconservation of Zebrafish sperm that comprises (a) removing the testes from the body cavity of a male Zebrafish; (b) isolating sperm from the testes by flushing the testes isolated in step (a) with a cryoprotectant using a micropipette to yield a sperm suspension having a volume of less than 30 μl per fish; and (c) freezing said sperm suspension.

2. The method of claim 1, wherein prior to step (a) the male Zebrafish is anaesthetized, dried, and/or decapitated.

3. The method of claim 1, wherein the amount of cryoprotectant used in step (b) is from 10 to 25 μl.

4. The method according to claim 3, wherein the amount of cryprotectant used in step (b) is from 17 to 22 μl.

5. The method of claim 1, wherein the cryoprotectant is a modified 1× Ginzburg-Ringer-solution containing a polar organic solvent.

6. The method of claim 1, wherein the temperature of the cryoprotectant is from 0 to 10° C.

7. The method of claim 6, wherein the temperature of the cryoprotectant is from 2 to 5° C.

8. The method of claim 5, wherein the modified 1× Ginzburg-Ringer-solution contains 5 to 20 vol. % of the polar organic solvent and optionally contains 5 to 25 wt.-% of a concentrated protein.

9. The method of claim 8, wherein the modified 1× Ginzburg-Ringer-solution contains 10 to 17 vol. % of the polar organic solvent and optionally contains 10 to 20 wt.-% of a concentrated protein.

10. The method of claim 5, wherein the polar organic solvent is selected from methanol, DMSO, and ethanol.

11. The method of claim 10, wherein the polar solvent is methanol.

12. The method of claim 8, wherein the concentrated protein is selected from milk powder, soya and bovine serum albumin.

13. The method of claim 12, wherein the concentrated protein is milk powder.

14. The method according to claim 1, wherein prior to step (c) the sperm suspension is divided into 2 to 5 portions.

15. The method of claim 14, wherein the sperm suspension is divided into 5 μl portions.

16. The method of claim 14, wherein the portions are kept in glass capillaries.

17. The method according to claim 1, where in step (c) the sperm suspension is kept at −70° C. (±10° C.) for at least 30 minutes and is then cooled down to the temperature of liquid nitrogen.

18. The method of claim 1 wherein the micropipette is a 10 μl cristal tip.

* * * * *